United States Patent [19]
Mashita et al.

[11] Patent Number: 5,968,409
[45] Date of Patent: Oct. 19, 1999

[54] METHOD FOR PREPARING TRIMER OF α-METHYL STYRENE OR DERIVATIVES THEREOF

[75] Inventors: Kiyotaka Mashita; Atsushi Fujioka; Takayuki Saitoh, all of Hitachi; Akihiro Kobayashi; Fumiaki Kanega, both of Ichihara, all of Japan

[73] Assignee: Hitachi Chemical Co., Ltd., Tokyo, Japan

[21] Appl. No.: 09/115,376

[22] Filed: Jul. 13, 1998

[30] Foreign Application Priority Data

Jul. 14, 1997 [JP] Japan ................................. 9-187098

[51] Int. Cl.$^6$ ............................. C09K 3/00; C07C 15/46; C08F 12/08
[52] U.S. Cl. .................................. 252/182.18; 252/363.5; 585/435; 525/333.3
[58] Field of Search ........................... 252/182.18, 363.5, 252/364; 585/435; 525/333.3

[56] References Cited

U.S. PATENT DOCUMENTS

| | | | |
|---|---|---|---|
| 3,385,905 | 5/1968 | Smith et al. | 260/668 |
| 4,254,292 | 3/1981 | Shimizu et al. | 585/320 |

FOREIGN PATENT DOCUMENTS

| | | |
|---|---|---|
| 50-157343 | 12/1975 | Japan . |
| 57-10851 | 3/1982 | Japan . |
| 4-15771 | 3/1992 | Japan . |
| 8-12601 | 1/1996 | Japan . |
| 8-23029 | 3/1996 | Japan . |

OTHER PUBLICATIONS

Kawakami, Y.; Toyoshima, N.; Ando, T.; Yamashita, Y., "Cationic Oligomerization of α–Methylstyrene by Binary Metal Oxides$^1$," Polymer Journal, vol. 13, No. 10. pp. 947–953 (1981) JP.

Pepper, D.C., "Polymerization," Friedel–Crafts and Related Reactions II, Alkylation and Related Reactions, Part 2, 1964, pp. 1293–1304.

Higashimura, T., Hiza, M., Hasegawa, H., "Catalytic Difference between Oxo Acids and Metal Halides in the Cationic Oligomerization of Styrene," *Macromolecules*, vol. 12, No. 2, Mar.–Apr. 1979, pp. 217–222.

Heublein, G., Bauerfeind, D., Spange, S., Knoppel, G., Wondraczek, R. "Recent Advances in Understanding the Propagation Mechanism in Cationic Vinyl Polymerization," International Union of Pure and Applied Chemistry Macromolecular Division, 1984, pp. 69–75.

*Primary Examiner*—Shean C. Wu
*Attorney, Agent, or Firm*—Fish & Richardson P.C.

[57] ABSTRACT

A method for preparing a trimer of α-methyl styrene or derivatives thereof, wherein α-methyl styrene or derivatives thereof is added to an organic solvent comprising Lewis acid is provided. According to the method, the trimer of α-methyl styrene or derivatives thereof can be obtained in high yield.

20 Claims, No Drawings

METHOD FOR PREPARING TRIMER OF α-METHYL STYRENE OR DERIVATIVES THEREOF

A method for preparing trimer of α-methyl styrene or derivatives thereof.

BACKGROUND OF THE INVENTION

1. Field of the Invention

The present invention relates to a method for preparing trimer of α-methyl styrene or derivatives thereof.

2. Description of the Prior Art

There have been known many methods for preparing an oligomer of α-methyl styrene or derivatives thereof, including a method using silver fuluoroborate (Japanese Patent Unexamined Application, hereinafter referred to as "J.P.KO-KAI" No. Sho 50-157343), a method using an alkyl aluminum, a method using a salt of ultra strong acid (Japanese Patent Publication for Opposition Purpose, hereinafter referred to as "J.P.KOKOKU" No. Sho 57-10851), a method for treating α-methyl styrene in the presence of sulfonic acid type cation exchange resin under a given temperature (J.P.KOKOKU Hei 4-15771), a method for reacting α-methyl styrene with heteropoly acid in solid-liquid phase heterogeneous system in the absence of a solvent (J.P.KOKAI Hei 8-12601), a method using an oxygen-containing compound such as water, dihydric alcohol or ether as a reaction adjusting agent in the presence of a solid acid catalyst such as activated clay (J.P.KOKOKU Hei 8-23029).

Polymer Journal, vol. 13, No. 10, p. 947–953 (1981) discloses a method for preparing dimer and trimer of α-methyl styrene by cation polymerization of α-methyl styrene in the presence of binary metal oxide such as $Al_2O_3$—$TiO_2$.

SUMMARY OF THE INVENTION

Accordingly, an object of the present invention is to provide a method for preparing a trimer of α-methyl styrene or derivatives thereof, which permits the production thereof in a high yield.

Another object of the present invention is to provide a method for preparing a trimer of α-methyl styrene or derivatives thereof, which permits the stable production thereof in a high yield.

A still further object of the present invention is to provide a method for preparing a trimer of α-methyl styrene or derivatives thereof in a high yield more effectively.

According to an aspect of the present invention, there is provided a method for preparing a trimer of α-methyl styrene or derivatives thereof, wherein α-methyl styrene or derivatives thereof is added to an organic solvent comprising Lewis acid.

According to preferred embodiment of the present invention, a molar ratio of Lewis acid to the α-methyl styrene or derivatives thereof is 0.0005–0.1, and a reaction temperature is between −15° C. and 30° C.

Preferably the Lewis acid is $AlCl_3$.

DESCRIPTION OF THE PREFERRED EMBODIMENTS

α-methyl styrene or derivatives thereof used in the present invention include α-methyl styrene, m- or p-methyl-α-methyl styrene, m- or p-ethyl- α-methyl styrene, m- or p-isopropyl-α-methyl styrene with α-methyl styrene being preferred because it is easily available.

Lewis acids used in the present invention include $Al_2O_3$, $TiO_2$, $ZnCl_2$, $SnCl_4$, $TiCl_4$, $FeCl_3$, $BF_3$, $AlCl_3$ with $AlCl_3$ being preferred. The Lewis acid may be used alone, but it is preferably used in the form of a solution in nitro-substituted alkane such as $CH_3NO_2$(nitromethane); aromatic nitro compounds such as nitrobenzene, o-nitro-toluene, m-nitro-toluene so that the reaction system becomes homogenous. In that case, a concentration of the Lewis acid in the solution is preferably 5–25% by weight. This is because if the concentration of the Lewis acid is lower than 5% by weight, the speed of the reaction will decrease, while if it exceeds 25% by weight, it will be difficult to dissolve the Lewis acid homogeneously.

It is essential in the method of the invention first to disperse or dissolve a catalyst, that is, Lewis acid such as $AlCl_3$, $AlCl_3$—$CH_3NO_2$, or $AlCl_3$—$C_6H_5NO_2$ in an organic solvent to prepare a solution of the acid in the solvent and then to add dropwisely α-methyl styrene or derivatives thereof (which may be dissolved in an organic solvent). If α-methyl styrene or derivatives thereof and the Lewis acid are mixed simultaneously in the organic solvent, or the Lewis acid or the Lewis acid dispersed or dissolved in the organic solvent is dropped into α-methyl styrene or derivatives thereof, or the organic solvent solution of the α-methyl styrene or derivatives thereof, the yield of a trimer of α-methyl styrene or derivatives thereof becomes low.

A molar ratio of Lewis acid to α-methyl styrene or derivatives is preferably 0.0005–0.1, more preferably 0.001–0.05, and most preferably 0.002–0.01. This is because if the molar ratio of the Lewis acid is lower than 0.0005, the speed and the rate of the reaction will decrease. While if it exceeds 0.1, the yield of the trimer will decrease.

A reaction temperature is typically from −15 to 30° C., preferably −10 to 20° C., more preferably −10 to 10° C. This is because if the reaction temperature is lower than −15° C., the yield of the tetramer or higher oligomers which comprise more than four units of α-methyl styrene or derivatives thereof increases, and the yield of the trimer decreases. While if it exceeds 30° C., the yield of the dimer of α-methyl styrene or derivatives thereof increases, and the yield of the dimer decreases.

Organic solvents used in the reaction include saturated aliphatic hydrocarbon such as petroleum ether, hexane and methyl cyclohexane; aromatic hydrocarbon such as benzene, toluene and xylene; ether or derivatives thereof such as diethyl ether, dibutyl ether and tetrahydrofuran.

If α-methyl styrene is used, a dimer of the formula (I) and a trimer of the formula (II) and (III) are obtained.

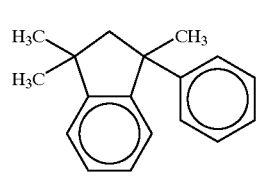

(I)

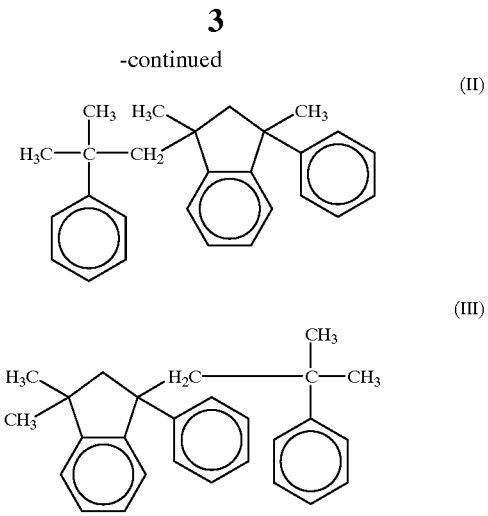

The trimer usually obtained is a mixture of the compound of the formula (II) and the compound of the formula (II) in a molar ratio of about 7:3.

The foregoing chemical structures are confirmed by NMR (nuclear magnetic resonance), HPLC (high pressure liquid chromatography), GC-MS analysis (gas chromatography—mass spectrometry), etc.

The trimer of α-methyl styrene or derivatives thereof obtained by the method according to the present invention can be used for various purposes such as a plasticizer for sealing materials and heat medium etc.

The present invention will hereinafter be described in more detail with reference to the following working Examples, but the present invention is not restricted to these specific Examples.

EXAMPLE 1

To a four-necked 200 ml-volume flask equipped with a stirring machine, a dropping funnel, a Dimroth condenser and a thermometer, there was placed a solution of 0.46 g of $AlCl_3$ in $CH_3NO_2$ (0.069 g of $AlCl_3$=0.517 mmol)(15% by weight) as Lewis acid, and 100 ml of toluene as an organic solvent. Then a toluene solution containing 30 g (254 mmol) of α-methyl styrene was placed in the dropping funnel (a molar ratio of $AlCl_3$ to α-methyl styrene is 0.002).

The temperature in the flask was kept to 0° C., the toluene solution containing α-methyl styrene was dropwise added over 35 minutes into the flask with stirring. The stirring of the reaction system was continued for 25 minutes after the dropwise addition was completed. Then, water was gradually dropwise added to decompose the Lewis acid. After the organic layer was washed with water, the product was analyzed by HPLC (high pressure liquid chromatography). Almost 100% of α-methyl styrene was reacted and a ratio of the trimer was as high as 75%. The result was shown in Table 1.

EXAMPLE 2

The same procedures as in Example 1 were repeated except that 0.913 g of $AlCl_3$ solution in $CH_3NO_2$ (15% by weight) was used (a molar ratio of $AlCl_3$ to α-methyl styrene was 0.004). The result was shown in Table 1.

EXAMPLE 3

The same procedures as in Example 1 were repeated except that 0.069 g of $AlCl_3$ was used instead of the $AlCl_3$ solution in $CH_3NO_2$. The reaction system was heterogeneous, however, the reaction progressed without problem. The result was shown in Table 1.

EXAMPLE 4

The same procedures as in Example 1 were repeated except that the reaction temperature was changed to 15° C. The result was shown in Table 1.

EXAMPLE 5

To a four-necked 200 ml-volume flask equipped with a stirring machine, a dropping funnel, a Dimroth condenser and a thermometer, there was placed a solution of 0.12 g of $AlCl_3$ in 0.40 g of nitrobenzene (0.12 g of $AlCl_3$=0.90 mmol)(23% by weight) as Lewis acid, and 100 ml of toluene as an organic solvent. Then a toluene solution containing 30 g (254 mmol) of α-methyl styrene was placed in the dropping funnel (a molar ratio of $AlCl_3$ to α-methyl styrene is 0.0035).

The temperature in the flask was kept at −7° C., the toluene solution containing α-methyl styrene was dropwise added over 48 minutes into the flask with stirring. The stirring of the reaction system was continued for 60 minutes after the dropwise addition was completed. Then, water was gradually dropwise added to decompose the Lewis acid. After the organic layer was washed with water, the product was analyzed by HPLC. Almost 100% of α-methyl styrene was reacted and a ratio of the trimer was as high as 75%. The result was shown in Table 1.

EXAMPLE 6

The same procedures as in Example 5 were repeated except that the temperature at the time of the stirring of 60 minutes was kept at 0° C. The result was shown in Table 1.

EXAMPLE 7

The same procedures as in Example 6 were repeated except that the concentration of $AlCl_3$ solution in nitrobenzene was changed to 10% by weight, and the amount of the $AlCl_3$ solution in nitrobenzene was 1.20 g. The result was shown in Table 1.

Comparative Example 1

The same procedures as in Example 1 were repeated except that 100 ml of a toluene solution containing 30 g of α-methyl styrene (254 mmol) was placed in the flask, then 0.46 g of $AlCl_3$ solution in $CH_3NO_2$ (15% by weight) and 50 ml of toluene were placed in the dropping funnel, and the catalyst ($AlCl_3$ solution in $CH_3NO_2$) was dropwise added into the α-methyl styrene solution (a molar ratio of $AlCl_3$ to α-methyl styrene was 0.002). The result was shown in Table 1.

The formation of dimer and trimer was confirmed by $^1$H-NMR analysis of fractions obtained from GC-MS analysis and HPLC.

TABLE 1

| | Molar ratio of $AlCl_3$ to α-methyl styrene | Reaction temperature (° C.) | Reaction rate (%) |
|---|---|---|---|
| Example 1 | 0.002 | 0 | 98.5 |
| Example 2 | 0.004 | 0 | 99.9 |

TABLE 1-continued

| | | | |
|---|---|---|---|
| Example 3 | 0.002 | 0 | 98.0 |
| | $CH_3NO_2$ not used | 0 | |
| Example 4 | 0.002 | 15 | 99.1 |
| Example 5 | 0.0035 | -7 | 99.9 |
| Example 6 | 0.0035 | 0 | 99.9 |
| Example 7 | 0.0035 | 0 | 99.9 |
| Comparative Example 1 | 0.002 catalyst was added into the monomer | 0 | 98.3 |

| | The ratio of the product (% of peak area in HPLC) | | | |
|---|---|---|---|---|
| | dimer | trimer | tetramer | pentamer and more |
| Example 1 | 15 | 75 | 8 | 2 |
| Example 2 | 18 | 75 | 5 | 2 |
| Example 3 | 21 | 73 | 3 | 3 |
| Example 4 | 21 | 72 | 6 | 1 |
| Example 5 | 7.5 | 75 | 15 | 2.5 |
| Example 6 | 24 | 70 | 5.5 | 0.5 |
| Example 7 | 8 | 70 | 17 | 5 |
| Comparative Example 1 | 33 | 45 | 12 | 10 |

As has been discussed above in detail, the method for preparing trimer of α-methyl styrene or derivatives thereof according to the present invention permits the production of the trimer of α-methyl styrene or derivatives thereof in high yield.

What is claimed is:

1. A method for preparing a trimer of a compound selected from the group consisting of alpha-methyl styrene, m- or p-methyl-α-methyl styrene, m- or p-ethyl-α-methyl styrene, and m- or p-isopropyl-α-methyl styrene, wherein the compound is added in a dropwise fashion to an organic solvent comprising Lewis acid, with the molar ratio of the Lewis acid to the compound being 0.0005–0.1, and a reaction temperature being about –15° C. to +30° C.

2. The method of claim 1, wherein the molar ratio of the Lewis acid to the compound is 0.001–0.05.

3. The method of claim 1, wherein the molar ratio of the Lewis acid to the compound is 0.002–0.01.

4. The method of claim 1, wherein the reaction temperature is between about –10° C. and about +20° C.

5. The method of claim 2, wherein the reaction temperature is between about –10° C. and about +20° C.

6. The method of claim 3, wherein the reaction temperature is between about –10° C. and about +20° C.

7. The method of claim 1, wherein the reaction temperature is between about –10° C. and about +10° C.

8. The method of claim 2, wherein the reaction temperature is between about –10° C. and about +10° C.

9. The method of claim 3, wherein the reaction temperature is between about –10° C. and about +10° C.

10. The method of claim 2, wherein the Lewis acid is $AlCl_3$.

11. The method of claim 3, wherein the Lewis acid is $AlCl_3$.

12. The method of claim 4, wherein the Lewis acid is $AlCl_3$.

13. The method of claim 5, wherein the Lewis acid is $AlCl_3$.

14. The method of claim 6, wherein the Lewis acid is $AlCl_3$.

15. The method of claim 7, wherein the Lewis acid is $AlCl_3$.

16. The method of claim 8, wherein the Lewis acid is $AlCl_3$.

17. The method of claim 9, wherein the Lewis acid is $AlCl_3$.

18. The method of claim 1, wherein the compound is alpha-methyl styrene.

19. The method of claim 9, wherein the compound is alpha-methyl styrene.

20. The method of claim 1, wherein the Lewis acid is $AlCl_3$.

* * * * *